(12) United States Patent
Daudet (10) Patent No.: US 12,097,646 B2
(45) Date of Patent: Sep. 24, 2024

(54) METHOD FOR MANUFACTURING AN ARTICULAR PROSTHESIS IMPLANT USING A CERAMIC IMPRINT

(71) Applicant: FX Shoulder Solutions, Viriat (FR)

(72) Inventor: Jean-Marie Daudet, Bourg-en-Bresse (FR)

(73) Assignee: FX Shoulder Solutions, Viriat (FR)

( * ) Notice: Subject to any disclaimer, the term of this patent is extended or adjusted under 35 U.S.C. 154(b) by 0 days.

(21) Appl. No.: 18/058,084

(22) Filed: Nov. 22, 2022

(65) Prior Publication Data

US 2023/0294337 A1 Sep. 21, 2023

(30) Foreign Application Priority Data

Nov. 26, 2021 (FR) ...................... 2112612

(51) Int. Cl.
| | |
|---|---|
| *B29C 43/36* | (2006.01) |
| *A61F 2/30* | (2006.01) |
| *B29C 43/00* | (2006.01) |
| *B29C 43/02* | (2006.01) |
| *B29C 43/52* | (2006.01) |
| *B29K 23/00* | (2006.01) |
| *B29K 71/00* | (2006.01) |
| *B29L 31/00* | (2006.01) |

(52) U.S. Cl.
CPC ............ *B29C 43/36* (2013.01); *A61F 2/3094* (2013.01); *B29C 43/003* (2013.01); *B29C 43/02* (2013.01); *B29C 43/52* (2013.01); *B29C 2043/366* (2013.01); *B29C 2043/3665* (2013.01); *B29K 2023/0683* (2013.01); *B29K 2071/00* (2013.01); *B29L 2031/7532* (2013.01)

(58) Field of Classification Search
CPC .......... A61F 2/3094; A61F 2002/30065; A61F 2002/30957; B29L 2031/7532; B29C 43/36; B29C 43/02; B29C 43/52; B29C 43/003; B29C 2043/366; B29C 2043/3665; B29C 43/006; B29K 2023/0683; B29K 2071/00
See application file for complete search history.

(56) References Cited

U.S. PATENT DOCUMENTS

| | | | | | |
|---|---|---|---|---|---|
| 4,747,990 | A | * | 5/1988 | Gaussens | ................ B29C 43/16 264/325 |
| 5,658,334 | A | * | 8/1997 | Caldarise | .................. B29B 9/12 623/923 |
| 5,721,334 | A | * | 2/1998 | Burstein | ............... B29C 43/006 264/126 |
| 5,849,068 | A | * | 12/1998 | Hofmann | ............... A61C 13/04 501/153 |

(Continued)

FOREIGN PATENT DOCUMENTS

| | | | |
|---|---|---|---|
| DE | 102007040893 A1 | 2/2009 | |
| FR | 2981277 A1 * | 4/2013 | ......... A61F 2/30767 |

(Continued)

*Primary Examiner* — Jerzi H Moreno Hernandez
(74) *Attorney, Agent, or Firm* — Defillo & Associates, Inc.; Evelyn A. Defillo (57) ABSTRACT

The invention relates to a method and a device for manufacturing an articular prosthesis implant using a mould comprising a ceramic imprint (1) moved by a piston (2), the ceramic imprint (1) pressing the thermoplastic material introduced into the mould.

7 Claims, 9 Drawing Sheets

(56) References Cited

U.S. PATENT DOCUMENTS

| | | | | |
|---|---|---|---|---|
| 2009/0155736 A1* | 6/2009 | Vekoerrer | ............ | A61C 13/206 |
| | | | | 433/34 |
| 2011/0035020 A1* | 2/2011 | Laughner | .............. | C04B 35/505 |
| | | | | 264/603 |
| 2021/0361434 A1* | 11/2021 | Zhang | ................... | A61F 2/3601 |

FOREIGN PATENT DOCUMENTS

| | | | | |
|---|---|---|---|---|
| FR | 3083693 A1 * | 1/2020 | ........... | A61F 2/3094 |
| WO | 9710010 A1 | 3/1997 | | |
| WO | 0217815 A1 | 3/2002 | | |

* cited by examiner

Fig. 1

COUPE A-A

COUPE B-B

METHOD FOR MANUFACTURING AN ARTICULAR PROSTHESIS IMPLANT USING A CERAMIC IMPRINT

CROSS-REFERENCE TO RELATED APPLICATIONS

The present application claims priority to French Patent Application No. 2112612, filed Nov. 26, 2021 which is hereby incorporated by reference herein in its entirety.

TECHNICAL FIELD

The invention relates to a method for manufacturing an articular prosthesis implant and a device for implementing said method.

BACKGROUND

The state of the art already describes methods for manufacturing articular prosthesis implants for which at least one part is obtained by moulding or overmoulding a thermoplastic material. To do this, the thermoplastic material is introduced into the mould cavity which is generally made of metal (for example stainless steel), to be moulded or overmoulded on a support element previously introduced into the mould of the implant. The flow of thermoplastic material required to obtain its final shape is generally produced by thermocompression or injection of the thermoplastic material in the mould cavity. One disadvantage of this manufacturing method is that the step of extracting the implant obtained is extremely difficult to implement due to the very high adhesion between the thermoplastic material and the metal cavity. Consequently, there is a risk that the implant extracted from the mould no longer respects the dimensions required before manufacture. There is also a risk that incorrect extraction of the implant so obtained will result in lower mechanical properties than those required before manufacture.

Consequently, a known solution to overcome this disadvantage consists in applying (before the step of moulding or overmoulding the thermoplastic material) a release agent to the mould cavity, so that the implant obtained can be extracted more easily and safely. Such a release agent is a chemical material known by those skilled in the art. However, this solution extends the duration of the implant manufacturing method since an additional step is required to apply the release agent to the cavity, which eventually increases the cost of manufacturing the implant produced (since the release agent is an expensive component). We must therefore consider methods for extracting the implant which are as good, without having to use such a release agent, especially in view of the current shortage of raw materials.

The invention aims in particular to propose a method for manufacturing an articular prosthesis implant and a device for implementing this method, which overcome all the above-mentioned disadvantages.

SUMMARY

The invention therefore relates to a manufacturing method comprising the following steps:
heating to a malleability temperature a thermoplastic material used to form at least partially the implant;
inside a mould cavity and using a ceramic imprint of the mould moved by a piston, pressing the thermoplastic material so that this material flows inside the mould cavity and takes the shape of the imprint;
allowing the thermoplastic material to cool down;
extracting the implant obtained from the mould.

Such a manufacturing method allows fast and safe production, while reducing the manufacturing costs since a release agent is no longer required. It also ensures that good-quality implants are obtained.

According to other optional characteristics of the method, taken alone or in combination:
the thermoplastic material is selected from ultra-high-molecular-weight polyethylene (UHMWPE) or polyetheretherketone (PEEK) or polyetherketoneketone (PEKK) and their derivatives;
a metal base, against which the thermoplastic material is pressed, is introduced into the mould cavity;
the ceramic is selected from alumina, composite, zirconia or oxynium.

The invention also relates to a device for manufacturing an articular prosthesis implant comprising:
at least a mould comprising a ceramic imprint;
at least a piston configured to move the ceramic imprint between at least two predefined positions, so that in one of these positions, the ceramic imprint presses a thermoplastic material previously introduced into the mould cavity and so that, in the other position, the ceramic imprint is not in contact with said thermoplastic material.

According to other optional characteristics of the device, taken alone or in combination:
the piston is made of ceramic;
the piston and the imprint form a monobloc element;
the ceramic is selected from alumina, composite, zirconia or oxynium;
the device comprises five moulds, each comprising a ceramic imprint and five pistons, each being configured to move one of said imprints.

BRIEF DESCRIPTION OF THE DRAWINGS

The invention will be better understood on reading the following description, given solely by way of example and with reference to the accompanying drawings in which.

DETAILED DESCRIPTION

Figure 1:
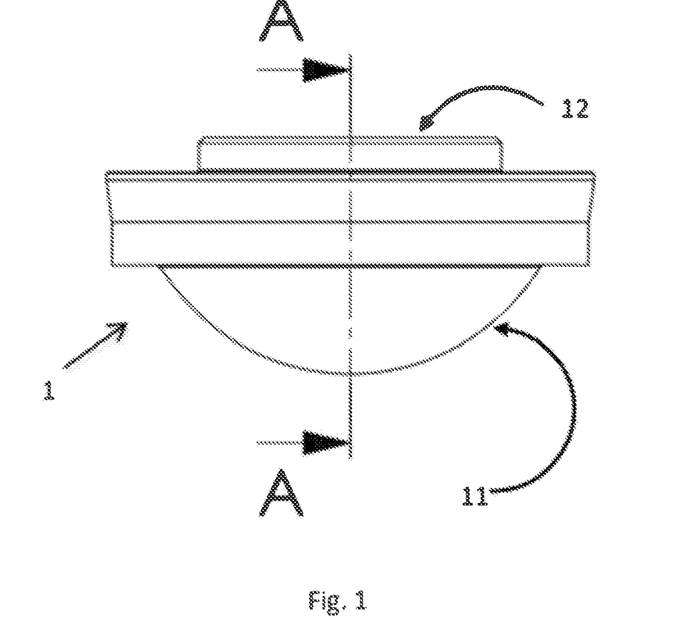
FIG. 1 is a side view of an imprint according to a first embodiment of the device according to the invention.
Figure 2:
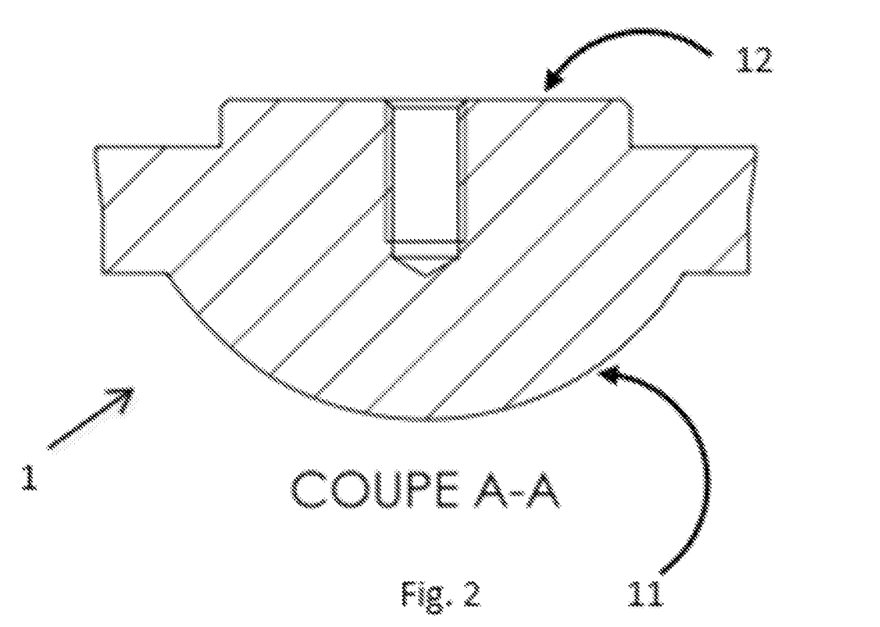
FIG. 2 is a cross-sectional view of the imprint shown on FIG. 1.
Figure 3:
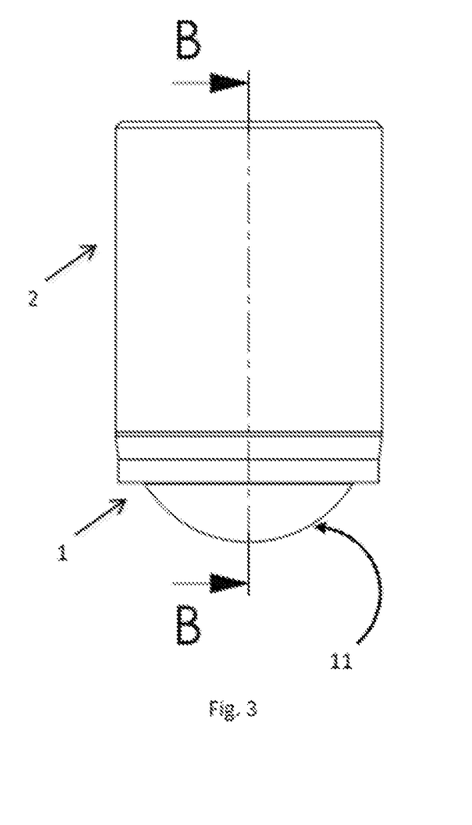
FIG. 3 is a side view of the imprint and of the piston according to the first embodiment of the device according to the invention.
Figure 4:
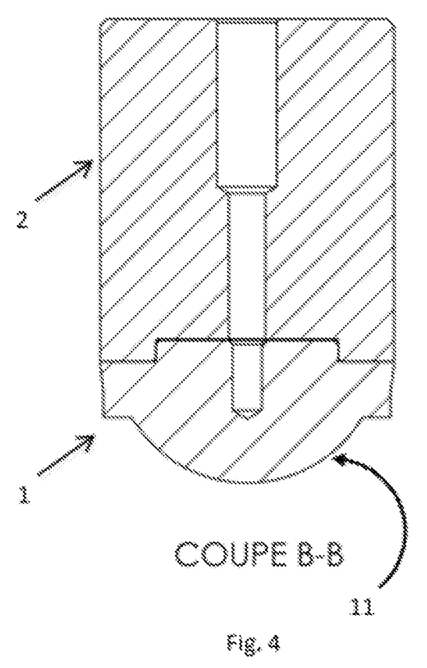
FIG. 4 is a cross-sectional view of the imprint and of the piston shown on FIG. 3.
Figure 5:
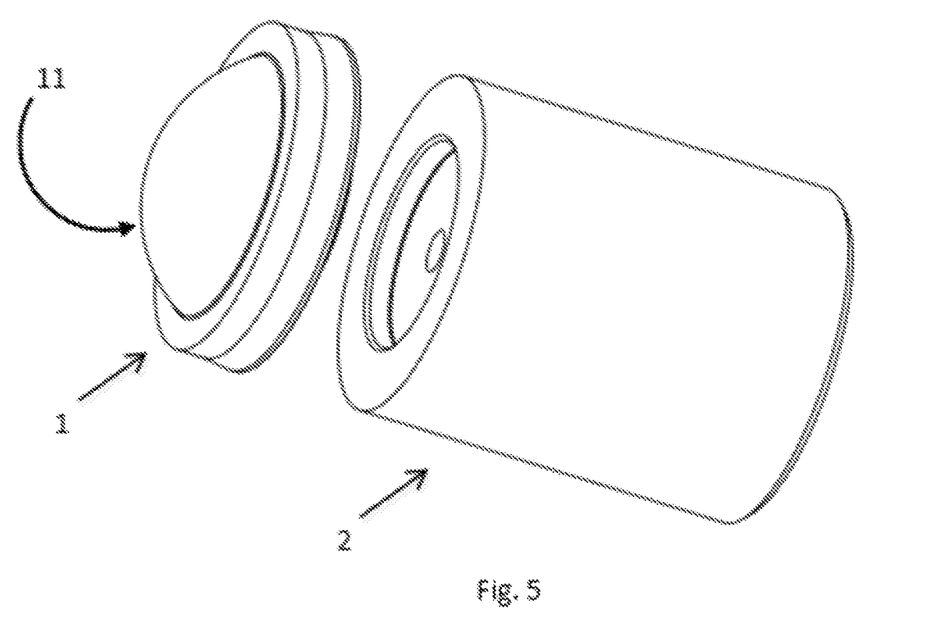
FIG. 5 is a perspective view of the imprint and of the piston shown on FIG. 3.
Figure 6:
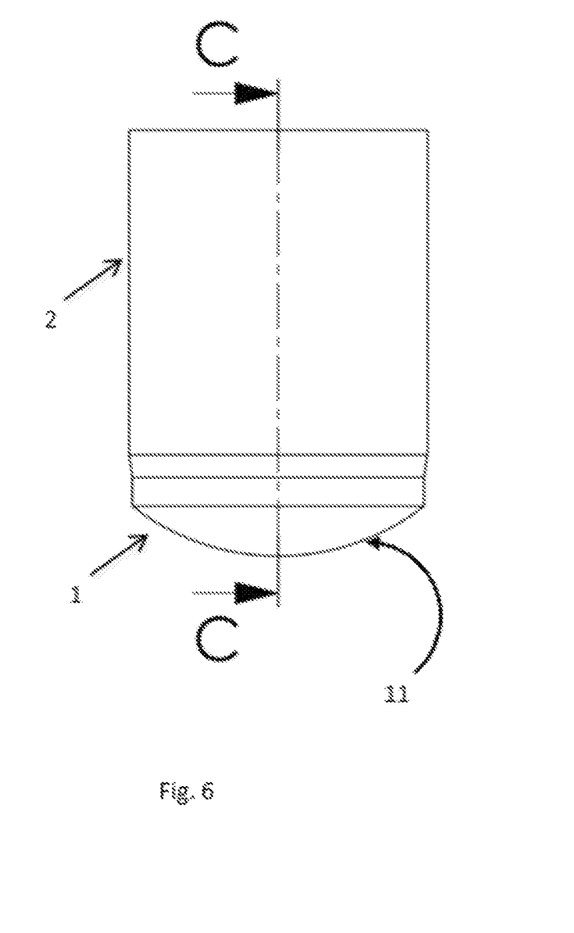
FIG. 6 is a side view of an imprint and of a piston according to a second embodiment of the device according to the invention.
Figure 7:
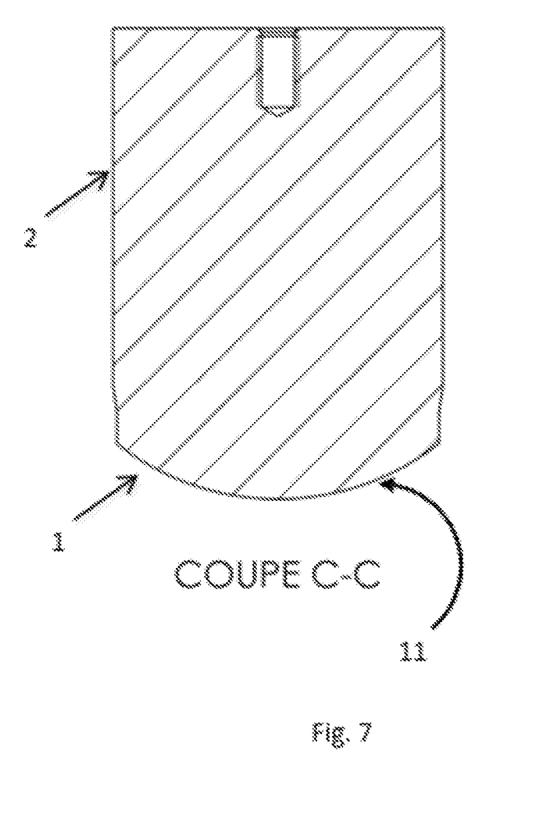
FIG. 7 is a cross-sectional view of the imprint and of the piston shown on FIG. 6.
Figure 8:
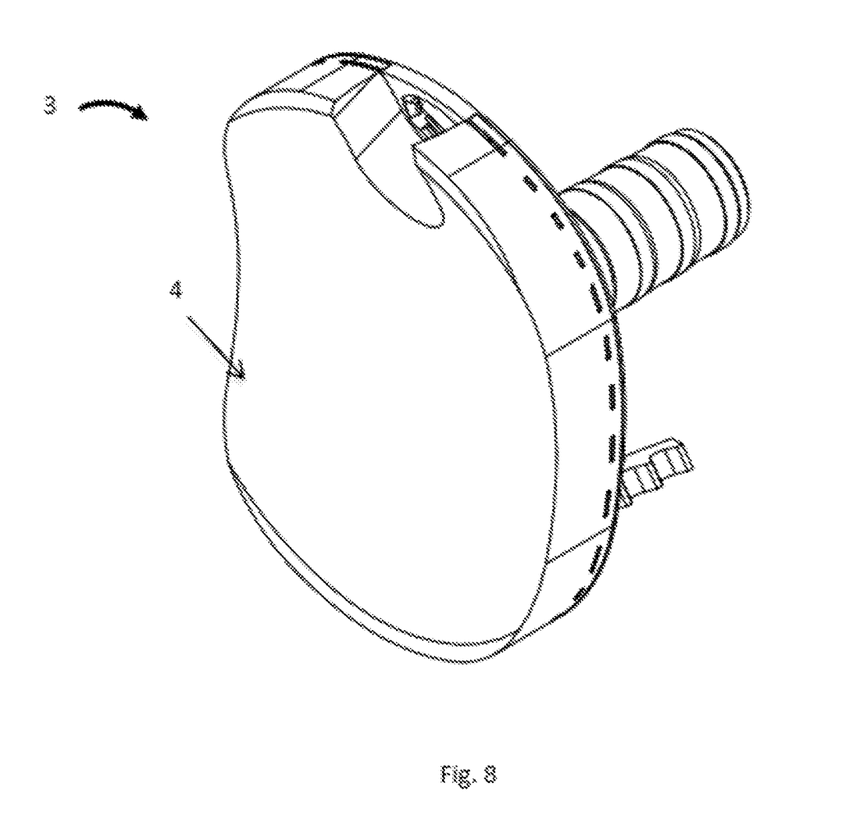
FIG. 8 is a perspective view of an articular prosthesis implant obtained.
Figure 9:
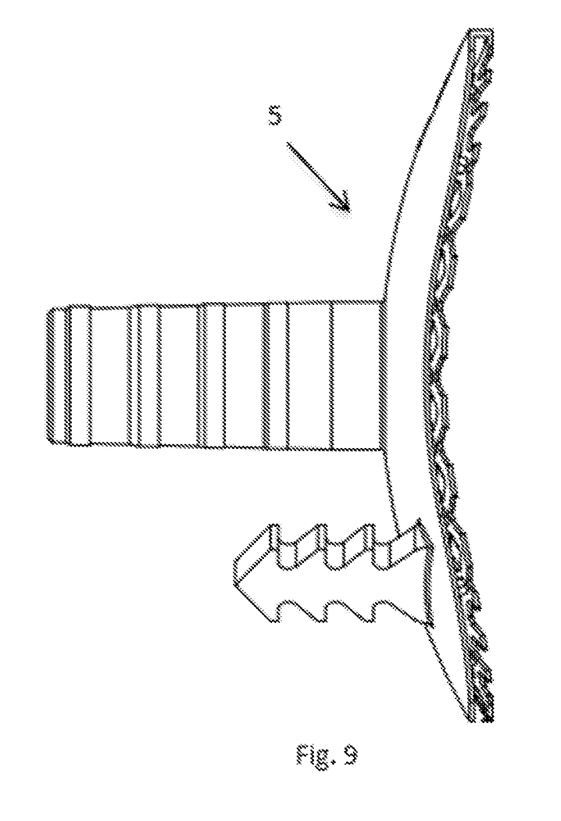
FIG. 9 is a side view of a metal base of the implant shown on FIG. 8.

FIGS. 1 to 7 show a ceramic imprint 1 and a piston 2 which are parts of the device for manufacturing an articular prosthesis implant according to the invention, an example of an implant 3 obtained being shown on FIGS. 8 and 9.

The device for manufacturing an articular prosthesis implant according to the invention comprises:
- at least a mould comprising a ceramic imprint 1;
- at least a piston 2 configured to move the ceramic imprint 1 between at least two predefined positions, so that in one of these positions, the ceramic imprint 1 presses a thermoplastic material previously introduced into the mould cavity and so that, in the other position, the ceramic imprint 1 is not in contact with said thermoplastic material.

The ceramic imprint 1 has a surface 11 intended to come into contact with the pressed thermoplastic material so as to form the articular implant 3. It also has a stop 12 against which the piston 2 presses when the imprint 1 is moved.

The piston 2 controls directly the movement of the ceramic imprint 1 inside the mould cavity so as to press the thermoplastic material to form at least partially the implant 3.

According to a second embodiment of the manufacturing device (FIGS. 6 and 7), the imprint 1 and the piston 2 are made of ceramic and are monobloc.

FIG. 8 shows an example of an implant 3 thus formed. According to this example, the pressed thermoplastic material forms the sliding plate 4 of the implant 3, this plate being overmoulded on a metal base 5 (FIG. 9) previously placed in the mould of the manufacturing device. As an alternative, it is quite possible to consider obtaining an implant made entirely from the pressed thermoplastic material inside the mould.

The device for manufacturing an articular prosthesis implant 3 according to the invention comprises the following steps:
- heating to a malleability temperature a thermoplastic material used to form at least partially the implant 3;
- inside a mould cavity and using a ceramic imprint 1 of the mould moved by a piston 2, pressing the thermoplastic material so that this material flows inside the mould cavity and takes the shape of the imprint 1;
- allowing the thermoplastic material to cool down;
- extracting the implant obtained from the mould.

Advantageously, when a metal base 5 is required to form the implant 3, the metal base 5 is introduced into the mould cavity and the thermoplastic material is pressed against this base.

Any type of thermoplastic material known by those skilled in the art can be used, for example: ultra-high-molecular-weight polyethylene (UHMWPE) or polyetheretherketone (PEEK) or polyetherketoneketone (PEKK) and their derivatives.

Any type of ceramic known by those skilled in the art can be used to form the imprint 1 and the piston 2, for example: alumina, composite, zirconia or oxynium.

The invention is not limited to the embodiments described and other embodiments will be clearly apparent to those skilled in the art.

I claim:

1. A method for manufacturing an articular prosthesis implant (3) comprising the following steps:
   heating to a malleability temperature a thermoplastic material used to form at least partially the articular prosthesis implant (3);
   pressing the thermoplastic material inside a cavity of a mould by using a ceramic imprint (1) moved by a piston (2), so that the thermoplastic material flows inside the cavity of the mould and takes the shape of the ceramic imprint (1);
   allowing the thermoplastic material to cool down;
   extracting the articular prosthesis implant (3) obtained from the cavity of the mould;
   wherein the ceramic imprint includes a ceramic surface designed to come in contact with the pressed thermoplastic material to form the articular prosthesis implant.

2. The method according to claim 1, wherein the thermoplastic material is selected from a material selected from the group consisting of ultra-high-molecular-weight polyethylene (UHMWPE), polyetheretherketone (PEEK), and polyetherketoneketone (PEKK).

3. The method according to claim 1, wherein a metal base (5), against which the thermoplastic material is pressed, is introduced into the cavity of the mould.

4. The method according to claim 1, wherein the ceramic imprint is made from a material selected from the group consisting of alumina, composite, zirconia, and ceramic zirconium oxide.

5. The method according to claim 1, wherein the piston and the ceramic imprint form a monobloc element.

6. The method according to claim 1, wherein the ceramic imprint includes a stop against which the piston presses during the movement of the ceramic imprint.

7. The method according to claim 1, further including the step of introducing a metal base into the cavity of the ceramic imprint prior to the pressing step, wherein the thermoplastic material is pressed against the metal base.

* * * * *